US00PP37659P2

(12) United States Plant Patent
Mathey

(10) Patent No.: US PP37,659 P2
(45) Date of Patent: Sep. 1, 2026

(54) ***CEPHALANTHUS* PLANT NAMED 'SMNCMBH'**

(50) Latin Name: *Cephalanthus occidentalis*
Varietal Denomination: SMNCMBH

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,642

(22) Filed: Nov. 8, 2025

(51) Int. Cl.
*A01H 6/76* (2018.01)
*A01H 5/02* (2018.01)

(52) U.S. Cl.
USPC ..... Plt./226

(58) Field of Classification Search
USPC ..... Plt./226
CPC ..... A01H 6/76; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Cephalanthus* plant named 'SMNCMBH', characterized by its compact, upright to somewhat outwardly spreading and uniformly mounding plant habit; vigorous growth habit; freely branching habit; glossy dark green-colored leaves; spherical head-type inflorescences with numerous white-colored flowers; reddish brown-colored fruits; and good garden performance and winter hardiness.

3 Drawing Sheets

Figure 1:
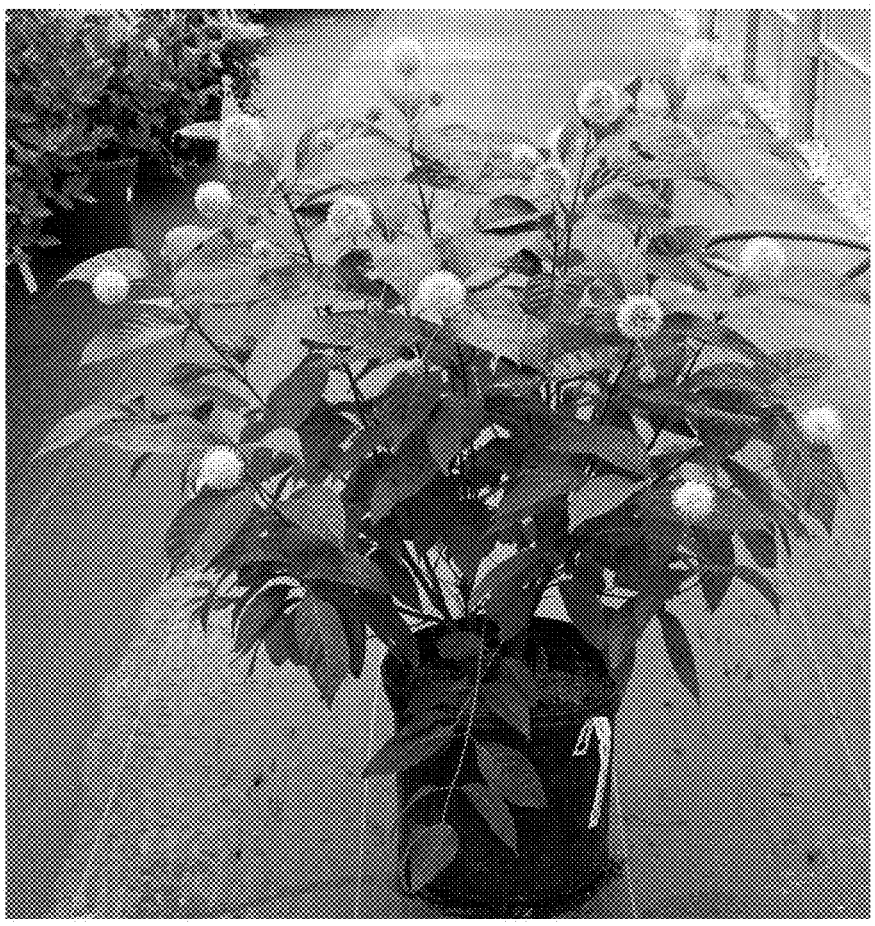

Botanical designation: *Cephalanthus occidentalis*.
Cultivar denomination: 'SMNCMBH'.

BACKGROUND OF THE INVENTION

The present invention relates to a new and distinct *Cephalanthus* plant, botanically known as *Cephalanthus occidentalis*, commonly called Buttonbush and hereinafter referred to by the name 'SMNCMBH'.

The new *Cephalanthus* plant is a product of a controlled breeding program conducted by the Inventor in Grand Haven, Michigan. The objective of the breeding program is to create compact, freely branching and freely flowering *Cephalanthus* plants.

The new *Cephalanthus* plant originated from an open-pollination during the summer of 2018 in Grand Haven, Michigan of a proprietary selection of *Cephalanthus occidentalis* identified as code No. S99, not patented, as the female, or seed, parent with an unknown proprietary selection of *Cephalanthus occidentalis* as the male, or pollen, parent. The new *Cephalanthus* plant was discovered and selected by the Inventor as a single flowering plant within the progeny of the stated open-pollination in a controlled environment in Grand Haven, Michigan during the summer of 2020.

Asexual reproduction of the new *Cephalanthus* plant by softwood cuttings in a controlled environment in Grand Haven, Michigan since the summer of 2020 has shown that the unique features of this new *Cephalanthus* plant are stable and reproduced true to type in successive generations of asexual reproduction.

SUMMARY OF THE INVENTION

Plants of the new *Cephalanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNCMBH'. These characteristics in combination distinguish 'SMNCMBH' as a new and distinct *Cephalanthus* plant:

1. Compact, upright to somewhat outwardly spreading and uniformly mounding plant habit.
2. Vigorous growth habit.
3. Freely branching habit.
4. Glossy dark green-colored leaves.
5. Spherical head-type inflorescences with numerous white- colored flowers with long-exerted pistils.
6. Reddish brown-colored fruits.
7. Good garden performance and winter hardiness.

Plants of the new *Cephalanthus* can be compared to plants of the female parent selection. Plants of the new *Cephalanthus* differ from plants of the female parent selection in the following characteristics:

1. Plants of the new *Cephalanthus* are denser and more tightly branched than plants of the female parent selection.
2. Plants of the new *Cephalanthus* are more mounding than plants of the female parent selection.
3. Leaves of plants of the new *Cephalanthus* are glossier than leaves of plants of the female parent selection.

Plants of the new *Cephalanthus* can be compared to plants of the *Cephalanthus occidentalis* 'SMCOSS', disclosed in U.S. Plant Pat. No. 26,543. In side-by-side comparisons, plants of the new *Cephalanthus* differ from plants of 'SMCOSS' in the following characteristics:

1. Plants of the new *Cephalanthus* are more compact and shorter than plants of 'SMCOSS'.

2. Plants of the new *Cephalanthus* are more uniformly mounding than plants of 'SMCOSS'.

BRIEF DESCRIPTION OF THE PHOTOGRAPHS

The accompanying colored photographs illustrate the overall appearance of the new *Cephalanthus* plant showing the colors as true as it is reasonably possible to obtain in colored reproductions of this type.

Colors in the photographs may differ slightly from the color values cited in the detailed botanical description which accurately describe the colors of the new *Cephalanthus* plant.

The photograph on the first sheet (FIG. 1) is a side perspective view of a typical flowering plant of 'SMNCMBH' grown in a container.

Figure 2:
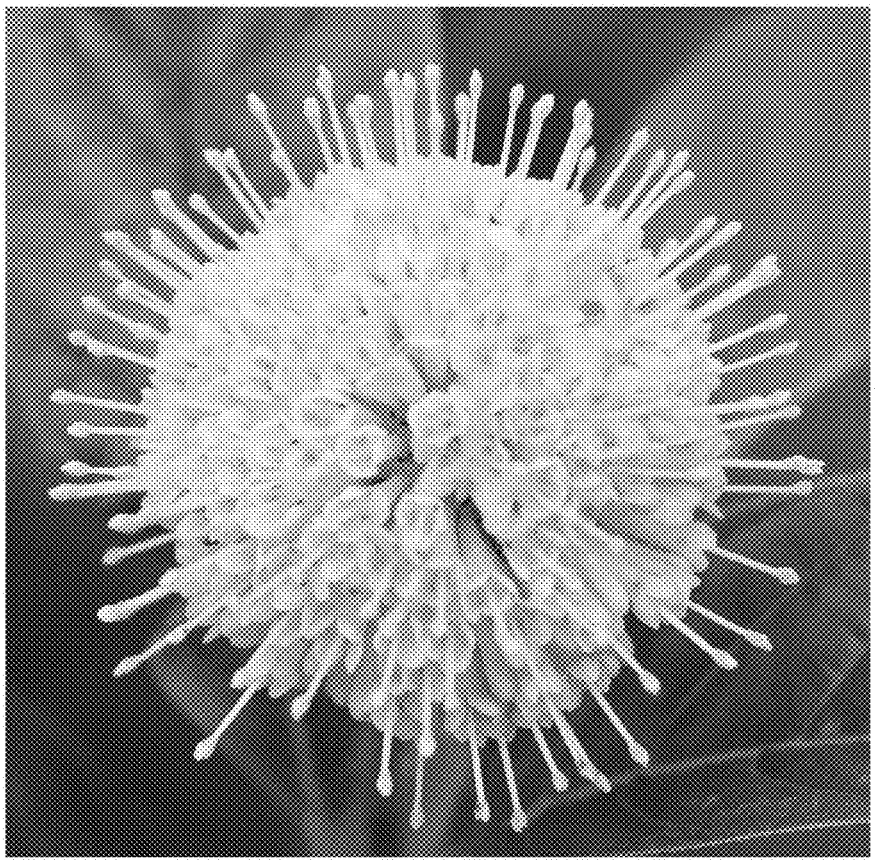

The photograph on the second sheet (FIG. 2) is a close-up view of a typical inflorescence of 'SMNCMBH'.

Figure 3:
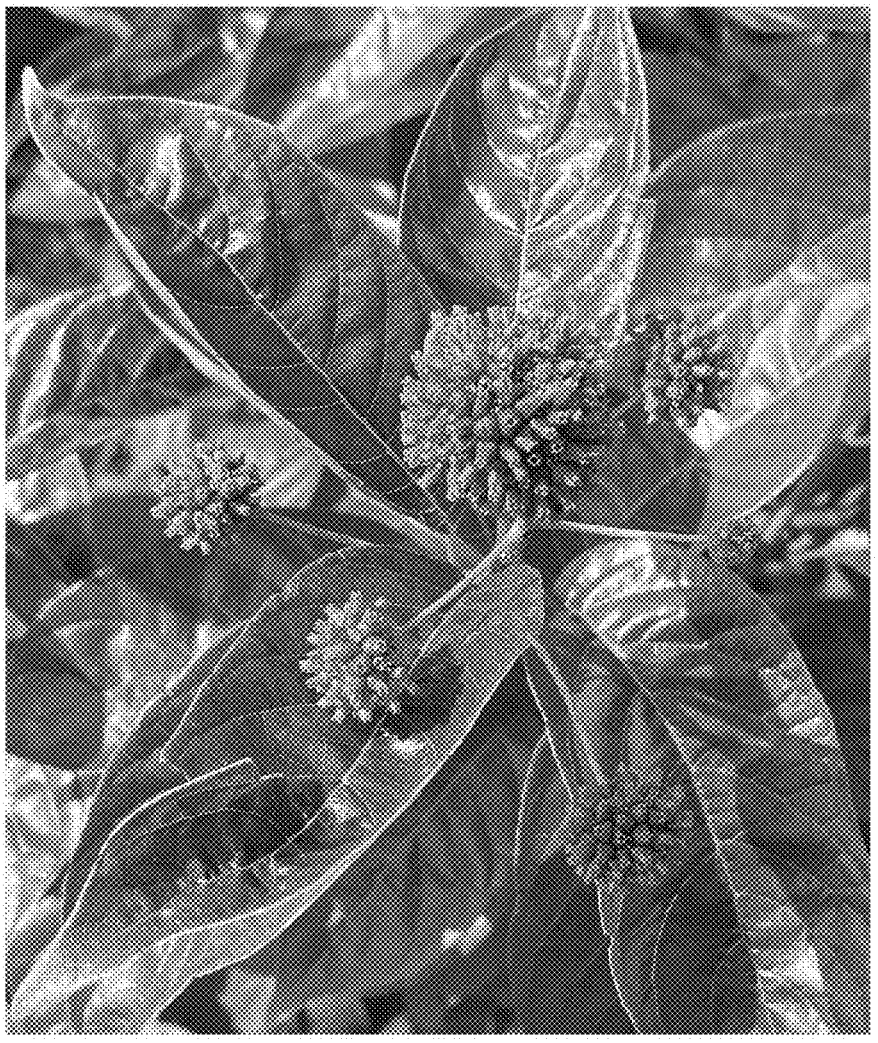

The photograph on the third sheet (FIG. 3) is a close-up view of typical leaves and developed fruits of 'SMNCMBH'.

DETAILED BOTANICAL DESCRIPTION

The following observations, measurements and values describe plants grown during the summer in three-gallon containers in a polyethylene-covered greenhouse in Grand Haven, Michigan and under cultural practices typical of commercial production. During the production of the plants, day temperatures ranged from 18° C. to 27° C. and night temperatures ranged from 5° C. to 10° C. Plants were three years old when the photographs and description were taken. In the description, color references are made to The Royal Horticultural Society Colour Chart, 2015 Edition, except where general terms of ordinary dictionary significance are used.

Botanical classification: *Cephalanthus occidentalis* 'SMNCMBH'.

Parentage:

*Female, or seed, parent.*—Proprietary selection of *Cephalanthus occidentalis* identified as code No. S99, not patented. Male, or pollen, parent: Unknown proprietary selection of *Cephalanthus occidentalis*, not patented.

Propagation:

*Type.*—By softwood cuttings.

*Time to initiate roots, summer.*—About 30 to 40 days at temperatures ranging from 18° C. to 27° C.

*Time to produce a rooted young plant, summer.*—About three months at temperatures ranging from 18° C. to 27° C.

*Root description.*—Medium in thickness; fibrous; typically white to brown in color, actual color of the roots is dependent on substrate composition, water quality, fertilizer, substrate temperature and physiological age of roots.

*Rooting habit.*—Freely branching; dense.

Plant description:

*Plant and growth habit.*—Perennial shrub; compact, upright to somewhat outwardly spreading and uniformly mounding plant habit; vigorous growth habit and moderate growth rate.

*Plant height, soil level to top of foliar plane.*—About 60 cm.

*Plant height, soil level to top of floral plane.*—About 65 cm.

*Plant diameter (area of spread).*—About 80 cm to 90 cm.

Lateral branch description:

*Branching habit.*—Freely branching habit with about five primary lateral branches each with about five to ten secondary lateral branches developing per plant.

*Length, primary lateral branches.*—About 50 cm.

*Diameter, primary lateral branches.*—About 8 mm.

*Length, secondary lateral branches.*—About 25 cm.

*Diameter, secondary lateral branches.*—About 4 mm.

*Internode length.*—About 5 cm.

*Strength.*—Strong, flexible.

*Aspect.*—About 10° to 30° from vertical.

*Texture and luster.*—Smooth, glabrous; semi-glossy.

*Color, developing.*—Close to 144A.

*Color, fully developed.*—Close to 198A.

Leaf description:

*Arrangement.*—Opposite, simple.

*Length.*—About 16 cm.

*Width.*—About 8 cm.

*Shape.*—Elliptic.

*Apex.*—Acuminate.

*Base.*—Broadly cuneate.

*Margin.*—Entire.

*Texture and luster, upper surface.*—Smooth, glabrous; somewhat coriaceous; glossy.

*Texture and luster, lower surface.*—Somewhat coriaceous with sparse pubescent along the midveins; matte.

*Venation pattern.*—Pinnate.

*Color.*—Developing leaves, upper and lower surfaces: Close to 146B slightly tinged with close to 165B. Fully expanded leaves, upper surface: Close to 147A; venation, close to 144A; in the autumn, leaves become closer to 160B with close to 162A and 173A to 173B. Fully expanded leaves, lower surface: Close to 147B; venation, close to 144A; in the autumn, leaves become closer to 160B with close to 162A and 173A to 173B.

*Petioles.*—Length: About 2.25 cm. Diameter: About 2 mm. Texture and luster, upper surface: Slightly pubescent; semi-glossy. Texture and luster, lower surface: Smooth, glabrous; semi-glossy. Color, upper surface: Close to 144A slightly tinged with close to 165A. Color, lower surface: Close to 144A.

Flower description:

*Flower appearance and arrangement.*—Single sessile tubular flowers arranged on dense terminal roughly spherical head-type inflorescences; heads roughly spherical in shape; freely flowering habit with more than 300 flowers per inflorescence and more than 50 inflorescences developing per plant during the flowering season; flowers face all directions depending on position on the head.

*Natural flowering season.*—Plants flower during June and July in Michigan.

*Flower longevity.*—Depending on temperature, individual flowers last about one to two weeks; flowers not persistent.

*Fragrance.*—Mildly fragrant; sweet and floral.

*Inflorescence height.*—About 3.5 cm.

*Inflorescence diameter.*—About 4 cm.

*Flower diameter.*—About 3 mm.

*Flower length (height).*—About 1 cm.

*Flower throat diameter.*—About 1 mm.

*Flower tube length.*—About 8 mm.

*Flower tube diameter, proximally.*—About 0.5 mm.

*Inflorescence buds.*—Length: About 1 cm. Diameter: About 1.25 cm. Shape: Globose. Texture and luster: Smooth, glabrous; matte. Color: Close to 144A.

*Petals.*—Quantity and arrangement: Four petals fused in a single tubular whorl. Length: About 1 mm. Width: About 1.5 mm. Shape: Elliptic. Apex: Rounded. Margin: Entire; not undulate. Texture and luster, upper and lower surfaces: Smooth, glabrous; matte. Color: When opening, upper and lower surfaces: Close to 155A. Fully opened, upper and lower surfaces: Close to 155A; venation, close to 155A; color does not change with subsequent development.

*Sepals.*—Quantity and arrangement: About four to five sepals arranged in a single whorl and fused at the base. Length: About 0.25 mm. Width: About 0.5 mm. Shape: Deltoid. Apex: Acute. Margin: Entire. Texture and luster: Smooth, glabrous; matte. Color, upper and lower surfaces: Close to 144A.

*Peduncles.*—Length: About 5 cm. Diameter: About 2 mm. Strength: Moderately strong. Aspect: Erect to about 45° from the stem axis. Texture and luster: Smooth, glabrous; matte. Color: Close to 144A.

*Reproductive organs.*—Androecium: Quantity per flower: About four; filaments are adnate to the flower throat. Anther size: About 0.5 mm by 0.1 mm. Anther shape: Linear. Anther color: Close to 165A. Amount of pollen: Moderate. Pollen color: Close to 10C. Gynoecium: Quantity per flower: One; pistils long-exerted. Pistil length: About 1.3 cm. Style length: About 1.25 cm. Style color: Close to 155A. Stigma diameter: About 0.5 mm. Stigma appearance: Globose. Stigma color: Close to 165A; at the apex, close to 145C. Ovary color: Close to 144A.

*Fruits.*—Type: Achene. Length: About 3 cm. Diameter: About 3 cm. Shape: Roughly spherical. Texture and luster: Glabrous; hard; matte. Color, developing: Close to 161C. Color, developed: Close to 165A.

*Seeds.*—Type: Nutlet. Quantity per fruit: One. Length: About 8 mm. Diameter: About 1.5 mm. Shape: Lanceolate. Texture and luster: Glabrous; matte. Color, immature: Close to 161C. Color, mature: Close to 165A.

Garden performance: Plants of the new *Cephalanthus* have been observed to have good garden performance and to tolerate rain, wind and suitable for USDA Hardiness Zones 4 to 10.

Pathogen & pest tolerance: To date, plants of the new *Cephalanthus* have not been observed to be tolerant to pathogens and pests common to *Cephalanthus* plants.

It is claimed:

1. A new and distinct *Cephalanthus* plant named 'SMNCMBH' as herein illustrated and described.

* * * * *